United States Patent
Schadt et al.

[11] Patent Number: 5,160,661
[45] Date of Patent: Nov. 3, 1992

[54] DIOXANYLPYRIDINE

[75] Inventors: Martin Schadt, Seltisberg; Alois Villiger, Basel, both of Switzerland

[73] Assignee: Hoffmann-La Roche Inc., Nutley, N.J.

[21] Appl. No.: 620,818

[22] Filed: Dec. 3, 1990

[30] Foreign Application Priority Data

Dec. 22, 1989 [CH] Switzerland .................. 4623/89

[51] Int. Cl.$^5$ .................. C09K 19/34; G02F 1/13; C07D 405/04
[52] U.S. Cl. .................. 252/299.61; 359/103; 546/268; 546/275
[58] Field of Search .................. 252/299.01, 299.61; 359/103; 544/333, 335; 546/268, 275

[56] References Cited

U.S. PATENT DOCUMENTS

| | | | |
|---|---|---|---|
| 4,668,425 | 5/1987 | Nigorikawa et al. | 252/299.61 |
| 4,726,911 | 2/1988 | Krause et al. | 252/299.61 |
| 4,774,020 | 9/1988 | Kitano et al. | 252/299.61 |
| 4,834,904 | 5/1989 | Krause et al. | 252/299.01 |
| 4,886,621 | 12/1989 | Sage et al. | 252/299.61 |
| 4,898,455 | 2/1990 | Buchecker et al. | 350/350 R |
| 4,913,837 | 4/1990 | Gray et al. | 252/299.61 |
| 5,112,934 | 4/1992 | Leenhouts et al. | 252/299.61 |

FOREIGN PATENT DOCUMENTS

| | | |
|---|---|---|
| 242716 | 10/1987 | European Pat. Off. |
| 314014 | 5/1989 | European Pat. Off. |
| WO86/06373 | 11/1986 | PCT Int'l Appl. |
| WO87/04158 | 7/1987 | PCT Int'l Appl. |
| 2161481 | 1/1986 | United Kingdom |

Primary Examiner—Robert L. Stoll
Assistant Examiner—Shean C. Wu
Attorney, Agent, or Firm—George M. Gould; George W. Johnston; Stephen L. Malaska

[57] ABSTRACT

Compounds of the formula

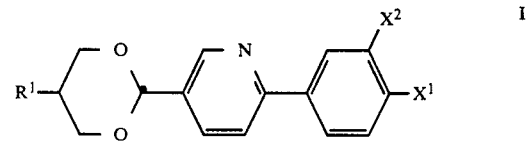

wherein $X^1$ represents fluorine or chlorine; $X^2$ denotes hydrogen, fluorine or chlorine; and $R^1$ signifies an alkyl group in which optionally a $>CH-CH<$ group is replaced by $>C=C<$ and/or a methylene group is replaced by oxygen, their manufacture, liquid crystalline mixtures which contain such compounds and their use for electro-optical purposes.

12 Claims, No Drawings

DIOXANYLPYRIDINE

BACKGROUND OF THE INVENTION

1. Field of the Invention

The present invention is concerned with novel dioxanylpyridines, their manufacture, liquid crystalline mixtures which contain these compounds as well as their use for electro-optical purposes.

2. Description

Liquid crystals are used primarily as dielectrics in indicating devices, since the optical properties of such substances can be influenced by an applied voltage. Electro-optical devices based on liquid crystals are well-known to a person skilled in the art and can be based on various effects. Examples of such devices are cells having dynamic scattering, DAP cells (deformation of aligned phases), guest/host cells, TN cells having a "twisted nematic" structure, STN cells ("supertwisted nematic"), SBE cells ("super birefringence effect") and OMI cells ("optical mode interference"). The most common indicating devices are based on the Schadt-Helfrich effect and have a twisted nematic structure.

The liquid crystal materials must have a good chemical and thermal stability and a good stability towards electric fields and electromagnetic radiation. Further, the liquid crystal materials should have low viscosity and in the cells should give short response times, low threshold potentials and a high contrast. Further, at the usual operating temperatures of about −30° C. to about +80° C., especially of about −20° C. to about +60° C., they should have a suitable mesophase, for example a nematic or cholesteric mesophase for the above-mentioned cells. Further properties such as the electrical conductivity, the dielectric anisotropy and the optical anisotropy must fulfil different requirements depending on the type of cell and field of application. For example, materials for cells having a twisted nematic structure should have a positive dielectric anisotropy and an electrical conductivity which is as low as possible. For some years there has been a particular interest in actively addressed liquid crystal displays, e.g. TFT applications ("thin film transistor") in television sets. However, the use of cyano compounds having a positive dielectric anisotropy in such displays generally leads to an undesired high increase in current.

Since liquid crystals are usually used as mixtures of several components, it is important that the components have a good miscibility with one another.

SUMMARY OF THE INVENTION

The present invention provides compounds of the formula

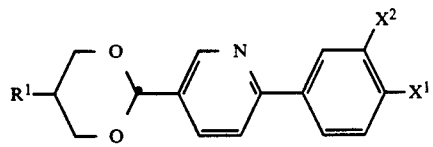

wherein $X^1$ is fluorine or chlorine; $X^2$ is hydrogen, fluorine or chlorine; and $R^1$ is an alkyl group in which optionally a >CH—CH< group is replaced by >C=C< and/or a methylene group is replaced by oxygen.

The compounds in accordance with the invention are liquid crystals with high clearing points. Moreover, highly ordered smectic phases are completely or largely suppressed. They have surprisingly low viscosities, especially low rotation viscosities, and have a good miscibility with usual liquid crystal materials. In spite of the relatively weak permanent dipole moments, they have remarkable large positive dielectric anisotropies. In this respect they are to some extent even comparable with bicyclic cyano compounds, which, however, have low clearing points and high viscosities and in TFT applications lead to conductivity problems. The compounds in accordance with the invention therefore facilitate low threshold potentials and at the same time short switching times.

The compounds in accordance with the invention are especially suitable as components of nematic and cholesteric mixtures and, by virtue of their good solubility in one another and in known liquid crystals, can also be used in comparatively high concentrations.

DETAILED DESCRIPTION OF THE INVENTION

The present invention provides compounds of the formula

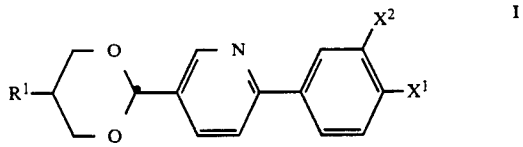

wherein $X^1$ is fluorine or chlorine; $X^2$ is hydrogen, fluorine or chlorine; and $R^1$ is alkyl, alkenyl, alkoxy, alkoxyalkyl, alkenyloxy, alkenyloxyalkyl or alkoxyalkenyl.

The compounds in accordance with the invention are liquid crystals with high clearing points. Moreover, highly ordered smectic phases are completely or largely suppressed. They have surprisingly low viscosities, especially low rotation viscosities, and have a good miscibility with usual liquid crystal materials. In spite of the relatively weak permanent dipole moments, they have remarkably large positive dielectric anisotropies. In this respect they are to some extent even comparable with bicyclic cyano compounds, which, however, have low clearing points and high viscosities and in TFT applications lead to conductivity problems. The compounds in accordance with the invention therefore facilitate low threshold potentials and at the same time short switching times.

The properties can be varied to a certain extent depending on the significance of the groups $R^1$, $X^1$ and $X^2$. Difluoro derivatives ($X^1 = X^2 = F$) give especially large dielectric anisotropies and comparatively short switching times. p-Chloro derivatives ($X^1 = Cl$) usually give high clearing points and similarly short switching times. 4-Alkenyl usually leads to lower threshold potentials and lower $k_{33}/k_{11}$ and 1E-alkenyl and 3E-alkenyl usually lead to shorter response times, higher $k_{33}/k_{11}$ and higher clearing points in comparison to alkyl residues $R^1$.

The term "alkyl groups in which optionally a >CH—CH< group is replaced by >C=C< and/or a methylene group is replaced by oxygen" embraces straight-chain and branched, optionally chiral, residues. These especially include alkyl of 1 to 12 carbon atoms, alkenyl of 2-12 carbon atoms (such as 1E-alkenyl, 3E-alkenyl, 4-alkenyl), alkoxy of 2-12 carbon atoms, alkoxyalkyl, alkenyloxy of 2 to 12 carbon atoms (such as 2E-alkenyloxy, 3-alkenyloxy) alkenyloxyalkyl of 2-12 carbon atoms (such as 2-alkenyloxymethyl) and the like. These moieties include methyl, ethyl, propyl, butyl, pentyl, hexyl, heptyl, octyl, nonyl, decyl, vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4-hexenyl, 4-heptenyl, methoxy, ethoxy, propyloxy, butyloxy, pentyloxy, hexyloxy, heptyloxy, methoxymethyl, ethoxymethyl, propyloxymethyl, allyloxy, 2E-butenyloxy, 2E-pentenyloxy, 3-butenyloxy, 3-pentenyloxy, allyloxymethyl and 2-butenyloxymethyl. Straight-chain residues are generally preferred.

Formula I embraces the compounds of the formulae

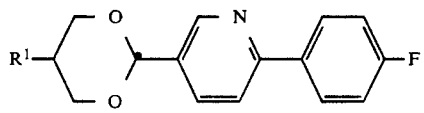 IA

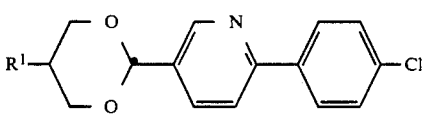 IB

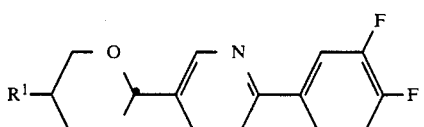 IC

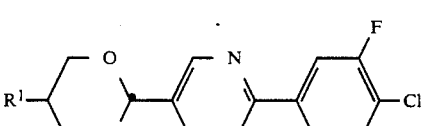 ID

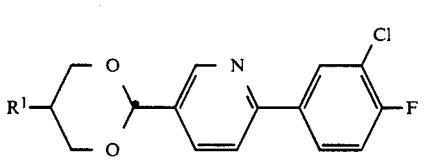 IE

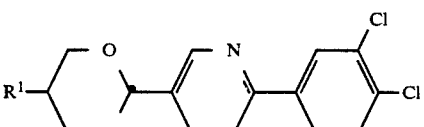 IF wherein $R^1$ has the above significance.

Preferably, $R^1$ has a maximum of 12 carbon atoms. Especially preferred residues $R^1$ are those with up to 7 carbon atoms, particularly those with up to 5 carbon atoms.

Preferably, $R^1$ signifies alkyl, 1E-alkenyl, 3E-alkenyl or 4-alkenyl, especially $C_1-C_{12}$-alkyl, $C_2-C_{12}$-1E-alkenyl, $C_4-C_{12}$-3E-alkenyl or $C_5-C_{12}$-4-alkenyl.

The compounds of formula I can be manufactured in accordance with the invention by reacting an aldehyde of the formula

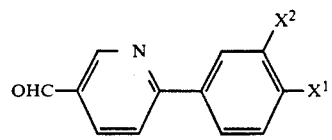 II or an acetal thereof with a compound of the formula

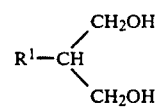 III wherein $R^1$, $X^1$ and $X^2$ have the above significances.

The reaction of the aldehyde of formula II or of a suitable acetal (e.g. the dimethyl acetal or ethylene acetal) with the diol of formula III can be effected in a manner known per se. Preferably, the reaction is effected in an inert organic solvent (for example, an aromatic hydrocarbon such as benzene, toluene or xylene) in the presence of a catalytic amount of an organic or inorganic acid such as p-toluene-sulphonic acid, sulphuric acid or dry hydrogen chloride. Temperature and pressure are not critical. However, the reaction is preferably carried out at atmospheric pressure and reflux temperature with the separation of the water which is formed.

The starting materials of formulae II and III are known compounds or analogues of known compounds and can be prepared according to known methods.

The compounds of formula I can be used in the form of mixtures with one another and/or with other liquid crystal components, such as e.g. with substances from the classes of Schiff's bases, azobenzenes, azoxybenzenes, phenylbenzoates, cyclohexanecarboxylic acid phenyl esters, cyclohexanecarboxylic acid cyclohexyl esters, biphenyls, phenylcyclohexanes, cyclohexylcyclohexanes, phenylpyrimidines, cyclohexylpyrimidines, phenyldioxanes, 2-cyclohexyl-1-phenylethanes, terphenyls, cyclohexyl-biphenyls, cyclohexlphenylpyrimidines and the like. Such substances are known to a person skilled in the art and many of them are, moreover, commercially available.

The liquid crystalline mixtures in accordance with the invention contain at least two components, of which at least one component is a compound of formula I. A second component and, if desired, further components can be additional compounds of formula I or other liquid crystal components. The compounds of formula I are especially suitable for nematic mixtures or, insofar as at least one component of the mixture is optically active, also for cholesteric mixtures.

Having regard to the good solubility of the compounds of formula I and having regard to their good miscibility with one another, the amount of these compounds in the mixtures in accordance with the invention can be relatively high. In general, however, an amount of about 1-50 wt. %, especially about 5-30 wt. %, of compounds of formula I is preferred.

The mixtures in accordance with the invention preferably contain, in addition to one or more compounds of formula I, one or more compounds from the group of compounds of the formula

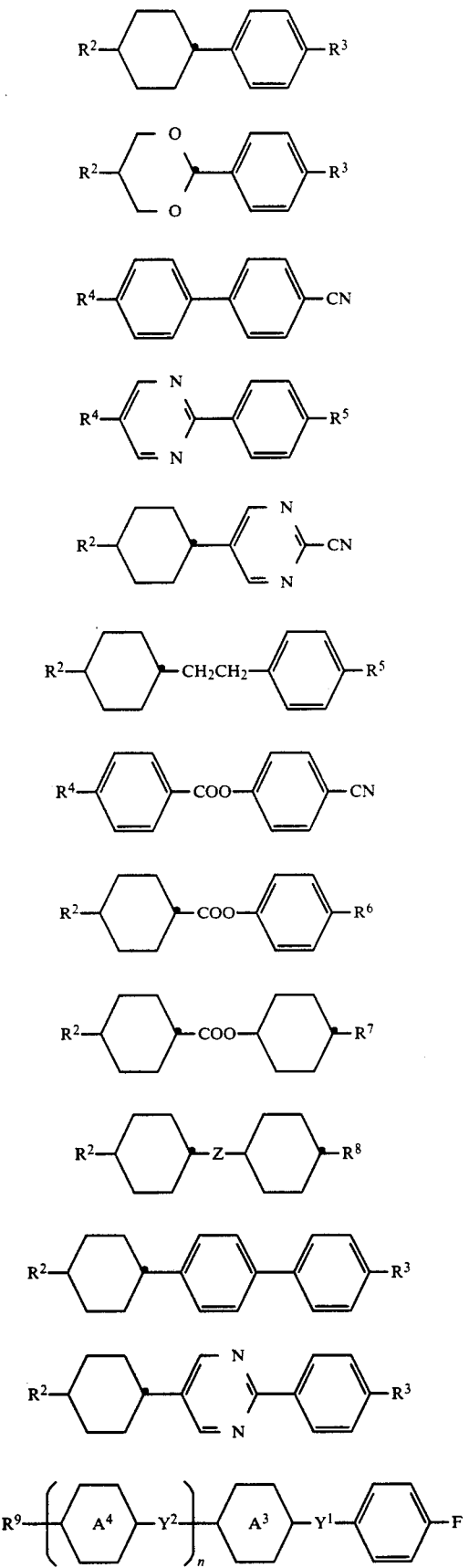
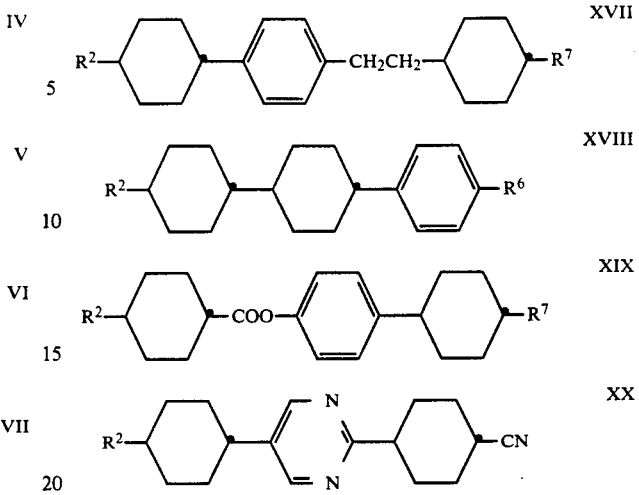

wherein $R^2$ and $R^7$ signify alkyl, 1E-alkenyl, 3E-alkenyl or 4-alkenyl; $R^3$ signifies cyano, -NCS, alkyl, 1E-alkenyl, 3E-alkenyl, 4-alkenyl, alkoxy, 2E-alkenyloxy or 3-alkenyloxy; $R^4$ signifies alkyl, 3E-alkenyl or 4-alkenyl; $R^5$ signifies cyano, -NCS, alkyl, 3E-alkenyl, 4-alkenyl, alkoxy, 2E-alkenyloxy or 3-alkenyloxy; $R^6$ signifies cyano, alkyl, 3E-alkenyl, 4-alkenyl, alkoxy, 2E-alkenyloxy or 3-alkenyloxy; Z signifies a single covalent bond or —CH$_2$CH$_2$—; $R^8$ signifies cyano, alkoxy, 2E-alkenyloxy, 3-alkenyloxy, alkyl, 1E-alkenyl, 3E-alkenyl, 4-alkenyl, alkoxymethyl or 2-alkenyloxymethyl; n stands for the number 0 or 1, one of the groups $Y^1$ and $Y^2$ signifies a single covalent bond, —COO—, —OOC—, —CH$_2$CH$_2$—, —CH$_2$O— or —OCH$_2$— and the other of the groups $Y^1$ and $Y^2$ signifies a single covalent bond; rings $A^3$ and $A^4$ each independently represent substituted or unsubstituted trans-1,4-cyclohexylene in which optionally 2 non-adjacent CH$_2$ groups are replaced by oxygen or substituted or unsubstituted 1,4-phenylene in which optionally 1 CH group or 2 CH groups is/are replaced by nitrogen; $R^9$ denotes alkyl, 1E-alkenyl or, when one of the groups $Y^1$ and $Y^2$ signifies a single covalent —COO—, —OOC— or —CH$_2$CH$_2$— and the other of the groups $Y^1$ and $Y^2$ signifies a single covalent bond, also 3E-alkenyl.

The alkyl, alkenyl, alkoxy and alkenyloxy residues $R^2$–$R^9$ in formulae IV–XX are preferably straight-chain residues. They preferably have up to 12, particularly up to 7, carbon atoms.

The mixtures in accordance with the invention can also contain optically active compounds (e.g. optically active 4'-alkyl- or 4'-alkoxy-4-biphenylcarbonitriles) and/or dichroic coloring substances (e.g. azo, azoxy or anthraquinone coloring substances). The amount of such compounds is determined by the solubility, the desired pitch, color, extinction and the like. In general, the amount of optically active compounds and dichroic coloring substances amounts to a maximum of in each case about 10 wt. % in the total mixture.

The manufacture of the mixtures in accordance with the invention and the manufacture of the electro-optical devices can be effected in a manner known per se.

The manufacture of the compounds of formula I as well as liquid crystalline mixtures containing these compounds are illustrated in more detail by the following Examples. C signifies a crystalline phase, $S_A$ signifies a smectic A phase, $S_B$ signifies a smectic B phase, N signifies a nematic phase and I signifies an isotropic phase. $V_{10}$ and $V_{50}$ denote the voltage for 10% and, respectively, 50% transmission, $t_{on}$ and $t_{off}$ denote the switching-on time and, respectively, the switching-off time and $\Delta n$ denotes the optical anistropy. $k_{11}$ and $k_{33}$ signify the elastic constants for splaying and, respectively, bending. $\Delta \epsilon$ denotes the dielectric anistropy, $\eta$ denotes the bulk viscosity and $\gamma_1$ denotes the rotation viscosity. The electro-optical properties were measured at 22° C. or at a temperature 10° C. below the clearing point. Unless indicated otherwise, the measurement was effected at 22° C. Unless indicated otherwise, the Examples were carried out as written.

EXAMPLE 1 a) A mixture of 44.3 g of 6-chloro-3-pyridinecarbinol, 300 ml of dioxan and 104.3 g of 3,4-dihydro-2H-pyran was treated with 3 g of p-toluenesulphonic acid monohydrate and stirred at 55° C. for 2 hours. The reaction mixture was treated with b 10 ml of diethylamine and, after cooling, taken up in diethyl ether. Repeated washing with water, drying over sodium sulphate and concentration in a vacuum yielded 87.3 g of crude 2-chloro-5-[(tetrahydro-2-pyranyloxy)methyl]pyridine.

b) A grignard reagent solution prepared from 1.53 g of magnesium, 10.5 g of 1-bromo-4-fluorobenzene and 70 ml of tetrahydrofuran was added dropwise at 3°-7° C. within 45 minutes to a mixture of 16.9 g of crude 2-chloro-5-[(tetrahydro-2-pyranyloxy)methyl]pyridine, 60 ml of tetrahydrofuran and 0.62 g of 1,3-bis(diphenylphosphino)-propanenickel-(II) chloride. The dark reaction mixture was stirred at 3° C. for a further 1 hr. and at room temperature for 2 hrs. and then extracted with 200 ml of diethyl ether and 120 ml of 0.5N ammonium chloride solution. The organic phase was washed neutral with water, dried over sodium sulphate, filtered and concentrated. Chromatographic purification of the residue on 230 g of silica gel with hexane/ethyl acetate (vol. 9:1) yielded 13.4 g of 2-(4-fluorophenyl)-5-[(tetrahydro-2-pyranyloxy)methyl]pyridine as a yellowish oil.

c) A solution of 13.4 g of 2-(4-fluorophenyl)-5-[(tetrahydro-2-pyranyloxy)methyl]pyridine in 250 ml of tetrahydrofuran was treated with 45 ml of 2N hydrochloric acid. The mixture was stirred at 60° C. overnight, then diluted with 100 ml of diethyl ether, washed once with 50 ml of saturated sodium carbonate solution and with two 60 ml portions of water, dried over sodium sulphate and concentrated. There were obtained 8.1 g of crude 6-(4-fluorophenyl)-3-pyridinecarbinol.

d) A solution of 8.1 g of 6-(4-fluorophenyl)-3-pyridinecarbinol in 200 ml of ethylene chloride was boiled for 7 hours with 13.1 g of activated manganese dioxide. The suspension was then filtered. Concentration of the filtrate and chromatographic purification of the residue on 150 g of silica gel with hexane/ethyl acetate (vol. 4:1) gave 6.2 g of 6-(4-fluorophenyl)-3-pyridine-carboxaldehyde as a brownish solid.

e) A solution of 1.51 g of 6-(4-fluorophenyl)-3-pyridinecarboxaldehyde and 1.10 g of 2-propyl-1,3-propanediol in 50 ml of toluene was treated with 10 drops of 10 percent (v/v) sulphuric acid. The mixture was heated to boiling for 1.5 hours, whereby moist toluene was distilled off and replaced by fresh toluene. Then, the reaction mixture was neutralized with triethylamine and, after cooling, washed three times with water, dried over sodium sulphate and concentrated. Chromatographic purification of the residue on 60 g of silica gel with toluene/acetone (vol. 99:1) and two-fold recrystallization of the trans/cis mixture from hexane/ethyl acetate (vol. 1:1) gave 0.51 g of pure 5-(trans-5-propyl-1,3-dioxan-2-yl)-2-(4-fluorophenyl)pyridine; m.p. (C-$S_A$) 106.5° C., $S_A$-N 117.5° C., cl.p. (N-I) 163° C.

The following compounds can be manufactured in an analogous manner:

5-(trans-5-ethyl-1,3-dioxan-2-yl)-2-(4-fluorophenyl)pyridine;

5-(trans-5-butyl-1,3-dioxan-2-yl)-2-(4-fluorophenyl)pyridine; m.p. (C-$S_A$) 86.0° C., $S_A$-N 138.5° C., cl.p. (N-I) 156° C;

5-(trans-5-pentyl-1,3-dioxan-2-yl)-2-(4-fluorophenyl)pyridine;

5-(trans-5-heptyl-1,3-dioxan-2-yl)-2-(4-fluorophenyl)pyridine;

5-(trans-5-vinyl-1,3-dioxan-2-yl)-2-(4-fluorophenyl)pyridine;

5-[trans-5-(1E-propenyl)-1,3-dioxan-2-yl]-2-(4-fluorophenyl)pyridine, m.p. (C-N) -138.4° C., cl.p. (N-I) 202° C;

5-[trans-5-(1E-butenyl)-1,3-dioxan-2yl]-2-(4-fluorophenyl)pyridine;

5-[trans-5-(1E-pentenyl)-1,3-dioxan-2-yl]-2-(4-fluorophenyl)pyridine;

5-[trans-5-(3-butenyl)-1,3-dioxan-2-yl]-2-(4-fluorophenyl)pyridine;

5-[trans-5-(4-pentenyl)-1,3-dioxan-2yl]-2-(4-fluorophenyl)pyridine;

5-(trans-5-ethyl-1,3-dioxan-2-yl)-2-(3,4-difluorophenyl)pyridine;

5-(trans-5propyl-1,3-dioxan-2-yl)-2-(3,4-difluorophenyl)pyridine, m.p. (C-$S_A$) 100.4° C., $S_A$-N 117.5° C., cl.p. (N-I) 125° C.;

5-(trans-5-butyl-1,3-dioxan-2yl)-2-(3,4-difluorophenyl)pyridine;

5-(trans-5-pentyl-1,3-dioxan-2-yl)-2-(3,4-difluorophenyl)pyridine;

5-(trans-5-heptyl-1,3-dioxan-2-yl)-2-(3,4-difluorophenyl)pyridine;

5-(trans-5-vinyl-1,3-dioxan-2-yl)-2-(3,4-difluorophenyl)pyridine;

5-[trans-5-(1E-propenyl)-1,3-dioxan-2-yl]-2-(b 3,4-difluorophenyl)pyridine, m.p. (C-$S_A$) 121° C., $S_A$-N 137° C., cl.p. (N-I) 159.5° C.;

5-[trans-5-(1E-butenyl)-1,3-dioxan-2-yl]-2-(3,4-difluorophenyl)pyridine;

5-[trans-5-(1E-pentenyl)-1,3-dioxan-2-yl]-2-(3,4-difluorophenyl)pyridine;

5-[trans-5-(3-butenyl)-1,3-dioxan-2-yl]-2-(3,4-difluorophenyl)pyridine;

5-[trans-5-(4-pentenyl)-1,3-dioxan-2-yl]-2-(3,4-difluorophenyl)pyridine;

5-(trans-5-ethyl-1,3-dioxan-2-yl)-2-(4-chlorophenylpyridine;

5-(trans-5-propyl-1,3-dioxan-2-yl)-2-(4-chlorophenyl)pyridine;

5-(trans-5-butyl-1,3-dioxan-2-yl)-2-(4-chlorophenyl)pyridine;

5-(trans-5-pentyl-1,3-dioxan-2-yl)-2-(4-chlorophenyl)pyridine;

5-(trans-5-heptyl-1,3-dioxan-2-yl)-2-(4-chlorophenyl)pyridine;

5-(trans-5-vinyl-1,3-dioxan-2-yl)-2-(4-chlorophenyl)pyridine;

5-[trans-5-(1E-propenyl)-1,3-dioxan-2-yl]-2-(4-chlorophenyl)pyridine;

5-[trans-5-(1E-butenyl)-1,3-dioxan-2-yl]-2-(4-chlorophenyl)pyridine;

5-[trans-5-(1E-pentenyl)-1,3-dioxan-2-yl]-2-(4-chlorophenyl)pyridine;
5-[trans-5-(3-butenyl)-1,3-dioxan-2-yl]-2-(4-chlorophenyl)pyridine;
5-[trans-5-(4-pentenyl)-1,3-dioxan-2-yl]-2-(4-chlorophenyl)pyridine;
5-(trans-5-propyl-1,3-dioxan-2-yl)-2-(4-chloro-3-fluorophenyl)pyridine;
5-(trans-5-butyl-1,3-dioxan-2-yl)-2-(4-chloro-3-fluorophenyl)pyridine;
5-(trans-5-pentyl-1,3-dioxan-2-yl)-2-(4-chloro-3-fluorophenyl)pyridine;
5-[trans-5-(1E-propenyl)-1,3-dioxan-2-yl]-2-(4-chloro-3-fluorophenyl)pyridine;
5-[trans-5-(1E-butenyl)-1,3-dioxan-2-yl]-2-(4-chloro-3-fluorophenyl)pyridine;
5-[trans-5-(1E-pentenyl)-1,3-dioxan-2-yl]-2-(4-chloro-3-fluorophenyl)pyridine;
5-[trans-5-(3-butenyl)-1,3-dioxan-2-yl]-2-(4-chloro-3-fluorophenyl)pyridine;
5-[trans-5-(4-pentenyl)-1,3-dioxan-2-yl]-2-(4-chloro-3-fluorophenyl)pyridine;
5-(trans-5-propyl-1,3-dioxan-2-yl)-2-(3,4-dichlorophenyl)pyridine;
5-(trans-5-butyl-1,3-dioxan-2-yl)-2-(3,4-dichlorophenyl)pyridine;
5-[trans-5-(1E-propenyl)-1,3-dioxan-2-yl]-2-(3,4-dichlorophenyl)pyridine.

EXAMPLE 2

Binary mixtures with 4-(trans-4-pentylcyclohexyl)-benzonitrile were prepared in order to investigate the properties of the compounds of formula I in mixtures. The threshold potential and the response times were measured in a TN cell (low bias tilt) having a plate separate of 8 μm; the 2.5-fold value of the threshold potential was selected as the operating voltage. The corresponding data for pure 4-(trans-4-pentylcyclohexyl)benzonitrile are: cl.p. (N-I) 54.6° C., $V_{10}=1.62$ V, $t_{on}=30$ ms, $t_{off}=42$ ms, $\Delta n=0.120$.

Mixture A 90 wt. % of 4-(trans-4-pentylcyclohexyl)benzonitrile,
10 wt. % of 5-(trans-5-propyl-1,3-dioxan-2-yl)-2-(4-fluorophenyl)pyridine;
 cl.p. (N-I) 59.4° C., $V_{10}=1.38$ V, $t_{on}=27$ ms, $t_{off}=43$ ms, $\Delta n=0.125$.

Mixture B 80 wt. % of 4-(trans-4-pentylcyclohexyl)benzonitrile,
20 wt. % of 5-(trans-5-propyl-1,3-dioxan-2-yl)-2-(4-fluorophenyl)pyridine;
 cl.p. (N-I) 66.4° C., $V_{10}=1.38$ V, $t_{on}=29$ ms, $t_{off}=48$ ms, $\Delta n=0.128$.

Mixture C 90 wt. % of 4-(trans-4-pentylcyclohexyl)benzonitrile,
10 wt. % of 5-(trans-5-propyl-1,3-dioxan-2-yl)-2-(3,4-difluorophenyl)pyridine;
 cl.p (N-I) 56.4° C., $V_{10}=1.33$ V, $t_{on}=28$ ms, $t_{off}=45$ ms, $\Delta n=0.122$.

Mixture D 80 wt. % of 4-(trans-pentylcyclohexyl)benzonitrile,
20 wt. % of 5-(trans-5-propyl-1,3-dioxan-2-yl)-2-(3,4-difluorophenyl)pyridine;
 cl.p (N-I) 58.8° C., $V_{10}=1.23$ V, $t_{on}=31$ ms, $t_{off}=55$ ms, $\Delta n=0.121$.

Mixture E 90 wt. % of 4-(trans-4-pentylcyclohexyl)benzonitrile,
10 wt. % of 5-[trans-5-(1E-propenyl)-1,3-dioxan-2-yl]-2-(4-fluorophenyl)pyridine;
 cl.p (N-I) 60.6° C., $V_{10}=1.41$ V, $t_{on}=27$ ms, $t_{off}=45$ ms, $\Delta n=0.126$.

Mixture F 80 wt. % of 4-(trans-4-pentylcyclohexyl)benzonitrile,
20 wt. % of 5-[trans-5-(1E-propenyl)-1,3-dioxan-2-yl]-2-(4-fuorophenyl)pyridine;
 cl.p. (N-I) 68.8° C., $V_{10}=1.41$ V, $t_{on}=29$ ms, $t_{off}=47$ ms, $\Delta n=0.124$.

Mixture G 90 wt. % of 4-(trans-4-pentylcyclohexyl)benzonitrile,
10 wt. % of 5-[trans-5-(1E-propenyl)-1,3-dioxan-2-yl]-2-(3,4-difluorophenyl)pyridine;
 cl.p. (N-I) 56.7° C., $V_{10}=1.34$ V, $t_{on}=29$ ms, $t_{off}=47$ ms, $\Delta n=0.125$.

Mixture H 80 wt. % of 4-(trans-4-pentylcyclohexyl)benzonitrile,
20 wt. % of 5-[trans-5-(1E-propenyl)-1,3-dioxan-2-yl]-2-(3,4-difluorophenyl)pyridine;
 cl.p. (N-I) 60.8° C., $V_{10}=1.24$ V, $t_{on}=34$ ms, $t_{off}=53$ ms, $\Delta n=0.128$.

We claim:

1. A compound of the formula

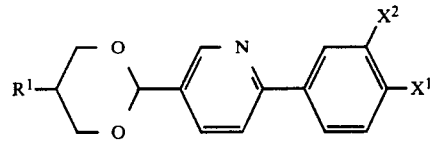

wherein $X^1$ is fluorine or chlorine, $X^2$ is hydrogen, fluorine or chlorine; and $R^1$ is alkyl of 1 to 12 carbon atoms, alkoxy of 2 to 12 carbon atoms, or $R^1$ is 1E-alkenyl, alkoxyalkenyl, alkenyloxyalkyl or alkyloxyalkenyl of 2 to 12 carbon atoms.

2. The compound according to claim 1, wherein $R^1$ is a straight-chain residue.

3. The compound according to claim 1, wherein $R^1$ has a maximum of 7 carbon atoms.

4. The compound according to claim 1, wherein $R^1$ is alkyl, 1E-alkenyl.

5. The compound according to claim 1, wherein $R^1$ is propyl, $X^1$ is fluorine and $X^2$ is hydrogen.

6. The compound according to claim 1, wherein $R^1$ is propyl ad $X^1$ and $X^2$ are fluorine.

7. The compound according to claim 1, wherein $R^1$ is 1E-propenyl, $X^1$ is fluorine and $X^2$ is hydrogen.

8. The compound according to claim 1, wherein $R^1$ is 1E-propenyl and $X^1$ and $X^2$ are fluorine.

9. A liquid crystalline mixture comprising at least two components, wherein at least one of said components is a compound of the formula

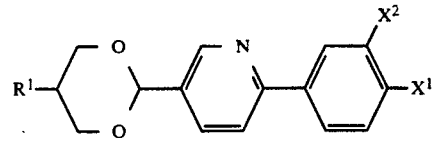

wherein $X^1$ is fluorine or chlorine, $X^2$ is hydrogen, fluorine or chlorine; and $R^1$ is alkyl of 1 to 12 carbon atoms, alkoxy of 2 to 12 carbon atoms, or $R^1$ is 1E-alkenyl, alkoxyalkenyl, alkenyloxyalkyl or alkyloxyalkenyl of 2 to 12 carbon atoms.

10. The liquid crystalline mixture according to claim 5, wherein the amount of compound I is about 1 to about 50% by weight of the mixture.

11. The liquid crystalline mixture of claim 6 wherein the amount of compound I is about 5 to about 30% by weight of the mixture.

12. An electro-optical cell comprising
(a) two plate means
(b) a liquid crystal means exposed between the two plate means and including a compound of the formula

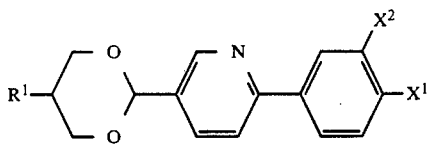

wherein $X^1$ is fluorine or chlorine, $X^2$ is hydrogen, fluorine or chlorine; and $R^1$ is alkyl of 1 to 12 carbon atoms, alkoxy of 2 to 12 carbon atoms, or $R^1$ is 1E-alkenyl, alkoxyalkenyl, alkenyloxyalkyl or alkyloxyalkenyl of 2 to 12 carbon atoms.

* * * * *